United States Patent
Chang et al.

(10) Patent No.: US 7,273,757 B2
(45) Date of Patent: Sep. 25, 2007

(54) RECOMBINANT VECTOR CONTAINING MJ1 GENE AND METHOD OF SITE-SPECIFIC INTEGRATION USING THE SAME

(75) Inventors: Hyo Ihl Chang, Seoul (KR); Hyo Sook Choi, Seoul (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 0 days.

(21) Appl. No.: 11/157,741

(22) Filed: Jun. 21, 2005

(65) Prior Publication Data

US 2006/0134788 A1    Jun. 22, 2006

(30) Foreign Application Priority Data

Dec. 16, 2004   (KR) ...................... 10-2004-0107077

(51) Int. Cl.
*C12N 15/90* (2006.01)
(52) U.S. Cl. .................................... 435/462; 435/320.1

(58) Field of Classification Search .................... None
See application file for complete search history.

(56) References Cited

OTHER PUBLICATIONS

Yang et al., Journal of Bacteriology, vol. 184, No. 7, 2002, pp. 1859-1864.*

* cited by examiner

*Primary Examiner*—James Ketter
(74) *Attorney, Agent, or Firm*—Clark & Elbing LLP (57) ABSTRACT

The present invention relates to a recombinant vector comprising MJ1 gene coding an integrase derived from *Enterococcus* temperate bacteriophage φ FC1 and an integration method using the vector. More particularly, the present invention relates to a recombinant vector comprising MJ1 gene which can make a site-specific integration in the human cell independently without other factors but not cause an excision and an integration method using the vector. Therefore, the present invention can be very useful in gene therapy in mammalian animal.

4 Claims, 9 Drawing Sheets

(3 of 9 Drawing Sheet(s) Filed in Color)

SEQUENCE LISTING

<160> NUMBER OF SEQ ID NOS: 4

<210> SEQ ID NO 1
<211> LENGTH: 1392
<212> TYPE: DNA
<213> ORGANISM: Bacteriophage FC1
<220> FEATURE:
<221> NAME/KEY: CDS
<222> LOCATION: (1)...(1392)

<400> SEQUENCE: 1

```
atg aaa cgt gca gca ttg tat ata cgt gta tcc aca atg gaa caa gcc      48
Met Lys Arg Ala Ala Leu Tyr Ile Arg Val Ser Thr Met Glu Gln Ala
 1               5                  10                  15 aag gaa gga tac agc att ccc gca caa aca gat aaa cta aaa gct ttt      96
Lys Glu Gly Tyr Ser Ile Pro Ala Gln Thr Asp Lys Leu Lys Ala Phe
             20                  25                  30 gca aaa gca aaa gat atg gca gtt gca aaa gta tat act gat cca ggg     144
Ala Lys Ala Lys Asp Met Ala Val Ala Lys Val Tyr Thr Asp Pro Gly
         35                  40                  45 ttt tca gga gca aaa atg gag cgc cct gca tta caa gaa atg ata tct     192
Phe Ser Gly Ala Lys Met Glu Arg Pro Ala Leu Gln Glu Met Ile Ser
     50                  55                  60 gat att caa aat aaa aaa att gat gtg gtt cta gtc tac aaa tta gac     240
Asp Ile Gln Asn Lys Lys Ile Asp Val Val Leu Val Tyr Lys Leu Asp
 65                  70                  75                  80 agg ctt tca cgt tca caa aag aat aca ttg tat tta att gaa gat gta     288
Arg Leu Ser Arg Ser Gln Lys Asn Thr Leu Tyr Leu Ile Glu Asp Val
                 85                  90                  95 ttt cta aaa aat aat gta gac ttt atc agc atg caa gaa agc ttt gac     336
Phe Leu Lys Asn Asn Val Asp Phe Ile Ser Met Gln Glu Ser Phe Asp
            100                 105                 110 aca tca aca cct ttt ggc cgt gcg acg ata gga atg tta tcc gtt ttt     384
Thr Ser Thr Pro Phe Gly Arg Ala Thr Ile Gly Met Leu Ser Val Phe
        115                 120                 125 gca caa tta gag cga gac aca att aca gaa aga atg cac atg gga aga     432
Ala Gln Leu Glu Arg Asp Thr Ile Thr Glu Arg Met His Met Gly Arg
    130                 135                 140 aca gaa cgt gca aaa caa gga tac tat cac gga agt ggc att gtt ccc     480
Thr Glu Arg Ala Lys Gln Gly Tyr Tyr His Gly Ser Gly Ile Val Pro
145                 150                 155                 160 tta ggt tac gat tat gtg cat gga gaa tta att atc aat gat tac gag     528
Leu Gly Tyr Asp Tyr Val His Gly Glu Leu Ile Ile Asn Asp Tyr Glu
                165                 170                 175 gcg caa att att caa gaa atc tat gat tta tat gtg aac caa ggt aaa     576
Ala Gln Ile Ile Gln Glu Ile Tyr Asp Leu Tyr Val Asn Gln Gly Lys
            180                 185                 190 gga cag caa tat ata aca aaa cgt atg gtt gca aaa tac cca gat aag     624
Gly Gln Gln Tyr Ile Thr Lys Arg Met Val Ala Lys Tyr Pro Asp Lys
        195                 200                 205 gta aaa aca tta acc ata gta aag tat gcc tta acc aat cca tta tat     672
Val Lys Thr Leu Thr Ile Val Lys Tyr Ala Leu Thr Asn Pro Leu Tyr
    210                 215                 220 att ggc aaa ata agt tgg gac ggc aaa gtg tat gat ggc cat cac tca     720
Ile Gly Lys Ile Ser Trp Asp Gly Lys Val Tyr Asp Gly His His Ser
```

```
                        225                 230                 235                 240
cct ata att gat aaa tct atg tac gat aaa gct caa gaa att att gcc       768
Pro Ile Ile Asp Lys Ser Met Tyr Asp Lys Ala Gln Glu Ile Ile Ala
                    245                 250                 255 aga atg gct caa aaa ggt ggc gaa cag cat gga aat caa tta ggg ctt       816
Arg Met Ala Gln Lys Gly Gly Glu Gln His Gly Asn Gln Leu Gly Leu
                260                 265                 270 tta tta ggg att act tat tgt ggt aaa tgc gga gct gaa gta ttt cgt       864
Leu Leu Gly Ile Thr Tyr Cys Gly Lys Cys Gly Ala Glu Val Phe Arg
            275                 280                 285 tat gta tca gga ggc aaa aaa tat cga tat aat tat tat atg tgt aga       912
Tyr Val Ser Gly Gly Lys Lys Tyr Arg Tyr Asn Tyr Tyr Met Cys Arg
        290                 295                 300 tca gta aag aaa atg cta cct tcg cta gta aaa gat tgg aac tgc aaa       960
Ser Val Lys Lys Met Leu Pro Ser Leu Val Lys Asp Trp Asn Cys Lys
305                 310                 315                 320 caa cct agt ctc aga caa gaa gta gtt gaa aag aaa gta ata gat tca      1008
Gln Pro Ser Leu Arg Gln Glu Val Val Glu Lys Lys Val Ile Asp Ser
                325                 330                 335 ctt aaa tca ttg gac ttc aaa aaa atc gaa cgt gaa tta aaa caa gtt      1056
Leu Lys Ser Leu Asp Phe Lys Lys Ile Glu Arg Glu Leu Lys Gln Val
            340                 345                 350 gaa aat aaa aca aaa tca aaa atc acc act att aat aac caa att tcc      1104
Glu Asn Lys Thr Lys Ser Lys Ile Thr Thr Ile Asn Asn Gln Ile Ser
        355                 360                 365 aag aag cat aac gaa aaa caa aaa att cta gat ttg tat caa tat ggt      1152
Lys Lys His Asn Glu Lys Gln Lys Ile Leu Asp Leu Tyr Gln Tyr Gly
    370                 375                 380 aca ttt gat gtc aca atg ctt aat gaa cgt atg aaa aaa att gat aat      1200
Thr Phe Asp Val Thr Met Leu Asn Glu Arg Met Lys Lys Ile Asp Asn
385                 390                 395                 400 gaa ata aat gcg tta act gcc aat ata gca aac tta gaa ggt acc aaa      1248
Glu Ile Asn Ala Leu Thr Ala Asn Ile Ala Asn Leu Glu Gly Thr Lys
                405                 410                 415 agt gag tca tta att aat aag ctt gaa acg tta aaa act ttt aat tgg      1296
Ser Glu Ser Leu Ile Asn Lys Leu Glu Thr Leu Lys Thr Phe Asn Trp
            420                 425                 430 gaa act gaa act aca gaa aat aaa atc ctt atc atc aaa gag ttt gtt      1344
Glu Thr Glu Thr Thr Glu Asn Lys Ile Leu Ile Ile Lys Glu Phe Val
        435                 440                 445 gaa cgt ata gaa cta ttt gat gat gag gta att att aaa tat aaa ttt      1392
Glu Arg Ile Glu Leu Phe Asp Asp Glu Val Ile Ile Lys Tyr Lys Phe
    450                 455                 460

<210> SEQ ID NO 2
<211> LENGTH: 464
<212> TYPE: PRT
<213> ORGANISM: Bacteriophage FC1

<400> SEQUENCE: 2

Met Lys Arg Ala Ala Leu Tyr Ile Arg Val Ser Thr Met Glu Gln Ala
 1               5                  10                  15

Lys Glu Gly Tyr Ser Ile Pro Ala Gln Thr Asp Lys Leu Lys Ala Phe
            20                  25                  30

Ala Lys Ala Lys Asp Met Ala Val Ala Lys Val Tyr Thr Asp Pro Gly
        35                  40                  45

Phe Ser Gly Ala Lys Met Glu Arg Pro Ala Leu Gln Glu Met Ile Ser
    50                  55                  60

Asp Ile Gln Asn Lys Lys Ile Asp Val Val Leu Val Tyr Lys Leu Asp
```

-continued

```
            65                  70                  75                  80
Arg Leu Ser Arg Ser Gln Lys Asn Thr Leu Tyr Leu Ile Glu Asp Val
                85                  90                  95
Phe Leu Lys Asn Asn Val Asp Phe Ile Ser Met Gln Glu Ser Phe Asp
                100                 105                 110
Thr Ser Thr Pro Phe Gly Arg Ala Thr Ile Gly Met Leu Ser Val Phe
                115                 120                 125
Ala Gln Leu Glu Arg Asp Thr Ile Thr Glu Arg Met His Met Gly Arg
                130                 135                 140
Thr Glu Arg Ala Lys Gln Gly Tyr Tyr His Gly Ser Gly Ile Val Pro
145                 150                 155                 160
Leu Gly Tyr Asp Tyr Val His Gly Glu Leu Ile Ile Asn Asp Tyr Glu
                165                 170                 175
Ala Gln Ile Ile Gln Glu Ile Tyr Asp Leu Tyr Val Asn Gln Gly Lys
                180                 185                 190
Gly Gln Gln Tyr Ile Thr Lys Arg Met Val Ala Lys Tyr Pro Asp Lys
                195                 200                 205
Val Lys Thr Leu Thr Ile Val Lys Tyr Ala Leu Thr Asn Pro Leu Tyr
210                 215                 220
Ile Gly Lys Ile Ser Trp Asp Gly Lys Val Tyr Asp Gly His His Ser
225                 230                 235                 240
Pro Ile Ile Asp Lys Ser Met Tyr Asp Lys Ala Gln Glu Ile Ile Ala
                245                 250                 255
Arg Met Ala Gln Lys Gly Gly Glu Gln His Gly Asn Gln Leu Gly Leu
                260                 265                 270
Leu Leu Gly Ile Thr Tyr Cys Gly Lys Cys Gly Ala Glu Val Phe Arg
                275                 280                 285
Tyr Val Ser Gly Gly Lys Lys Tyr Arg Tyr Asn Tyr Tyr Met Cys Arg
                290                 295                 300
Ser Val Lys Lys Met Leu Pro Ser Leu Val Lys Asp Trp Asn Cys Lys
305                 310                 315                 320
Gln Pro Ser Leu Arg Gln Glu Val Val Glu Lys Lys Val Ile Asp Ser
                325                 330                 335
Leu Lys Ser Leu Asp Phe Lys Lys Ile Glu Arg Glu Leu Lys Gln Val
                340                 345                 350
Glu Asn Lys Thr Lys Ser Lys Ile Thr Thr Ile Asn Asn Gln Ile Ser
                355                 360                 365
Lys Lys His Asn Glu Lys Gln Lys Ile Leu Asp Leu Tyr Gln Tyr Gly
                370                 375                 380
Thr Phe Asp Val Thr Met Leu Asn Glu Arg Met Lys Lys Ile Asp Asn
385                 390                 395                 400
Glu Ile Asn Ala Leu Thr Ala Asn Ile Ala Asn Leu Glu Gly Thr Lys
                405                 410                 415
Ser Glu Ser Leu Ile Asn Lys Leu Glu Thr Leu Lys Thr Phe Asn Trp
                420                 425                 430
Glu Thr Glu Thr Thr Glu Asn Lys Ile Leu Ile Lys Glu Phe Val
                435                 440                 445
Glu Arg Ile Glu Leu Phe Asp Asp Glu Val Ile Ile Lys Tyr Lys Phe
450                 455                 460
```

<210> SEQ ID NO 3
<211> LENGTH: 739
<212> TYPE: DNA
<213> ORGANISM: Bacteriophage FC1

```
<220> FEATURE:
<221> NAME/KEY: misc_feature
<222> LOCATION: 220
<223> OTHER INFORMATION: n = A,T,C or G

<400> SEQUENCE: 3
gaagatcttg ttctcgagca tagtctcctt caagttttgt tatatctgat aatagagact    60 tttcttttg ttgtaaacta ttgattgaca aatctggtcc tcctttaaaa tatataatta    120
atattggttt aattatacca ttctataggt aagaacagta atatgaccaa atttaaatat    180 cttttatgc actaatcaaa gttttcctta caagcatttn ttcaattacg agttgatttc    240
ttttattcaa atgaccatag acagctagtt cagattttc gggtagcatt agtaacatat    300
ttgctaattc gtatttggag acgatacagt ttatagtttc gtcctgtgtt actaatgaga    360
atcgaactag cattttggg tacatactta acattctaat cttttcaact actcctacat    420 aattagttt cataatatcg gcctcctagt aatacaatta taccgaatgc atgttcgtat    480
tgtctatagg tttgtataaa tgtaatattt taggtatatg attttgttta ttagtgtaaa    540
taacactatg tacctaaaat ttatatttaa taattacctc atcatcaaat agttctatac    600
gttcaacaaa ctctttgatg ataaggattt tattttctgt agtttcagtt tcccaattaa    660 aagttttaa cgtttcaagc ttattaatta atgactcact tttggtacct tctaagtttg    720
ctatattggc agttaacgc                                                739

<210> SEQ ID NO 4
<211> LENGTH: 290
<212> TYPE: DNA
<213> ORGANISM: Enterococcus faccalis KBL 707 strain

<400> SEQUENCE: 4
cggccattga attagggtgt cgaatttatc aaagtagtca aatcaaattt ggcaaagtta    60
cgtccagtca acaagtcgct caacgattac tccaagagat gaaggggctg caacaagaac    120
atttaatttg tatttacttg aataccaaga atgacattat ccaacagaaa acgattttca    180
aaggatcact gaatcaaagt attgctcatc cacgcgaaat ttttcgggaa gcggttaaat    240
attcttctgc tcgcatacta ttagctcata atcatccatc tggcaatccg              290
```

RECOMBINANT VECTOR CONTAINING MJ1 GENE AND METHOD OF SITE-SPECIFIC INTEGRATION USING THE SAME

CROSS-REFERENCE TO RELATED APPLICATIONS

The present application claims the benefit of Korean Patent Application No. 10-2004-0107077, filed on Dec. 16, 2004, in the Korean Intellectual Property Office, the disclosure of which is incorporated in its entirety by reference.

BACKGROUND OF THE INVENTION

1. Field of the Invention

The present invention relates to a recombinant vector containing MJ1 gene coding an integrase derived from *Enterococcus* temperate bacteriophage φ FC1 and an integration method using the vector. More particularly, the present invention relates to a recombinant vector containing MJ1 gene which can make a site-specific integration in the human cell independently without other factors but not cause an excision and an integration method using the vector.

2. Description of Related Art

*Enterococcus faecalis* is a gram-positive anaerobic bacterium that normally occurs in the intestines of most animal from cockroaches to humans. *E.faecalis* KBL703 strain and its temperate phage φ FC1 was first isolated in our laboratory from a culture of the lysogenic strain of KBL703 following induction by UV irradiation (Kim et al., (1994) Mol. Cell., 4, 155-158). Bacteriophage φ FC1 has double-stranded DNA genome of approximately 40.5 Kbp, icosahedral head and a sheathless noncontractile tail. Phage φ FC1 integration into the host chromosome occurs by a site-specific mechanism. A gene that encodes a site-specific integrase, MJ1, and that is upstream of the attP site has been identified. MJ1 encodes a 465-amino-acid polypeptide with similarity in its N-terminal domain to site-specific integrases. Analysis of the DNA sequences around the attP region identified two predicted bacterium-phage junction regions (attL and attR). The corresponding bacterial attachment site (attB) was deduced from the sequences of these regions (Kim et al., (1996) Biochem. Mol. Biol, 29, 448-45412).

Integrase MJ1 mediates unidirectional site-specific integration between two DNA recognition sequences which is the phage attachment site, attP, and the bacterial attachment site, attB. To accomplish integration, temperate phage ΦFC1 encodes an integrase MJ1 that mediates integration between attP and attB. In 290 bp attB sequences, attB site has 3 bp conserved core sequences, which overlapped with 3 bp conserved core sequences of 730 bp attP. Centering around core sequences, attP and attB share their sequences in half, which become attL and attR and 3 bp core sequences is repeated (Yang et al., (2002) J. Bacteriol., 184, 1859-1864).

In gene therapy, vectors are the vehicles that are used to transfer the gene of interest to the target cells. Unfortunately, there is no such thing as a 'good universal vector,' all of the vectors that are currently available have both advantages and disadvantages. For example, one viral vector might be able to enter target cells very efficiently but once there invokes a strong immune response, resulting in that cell being killed by the immune system, so begin to have problem with safety in host. Accordingly, it is clear that the previously distinct boundaries between viral and non-viral vectors are becoming increasingly blurred. From these reasons, development of safe integration system into implored gene is very important. However, cruder methods prevail for placement of the introduced gene into the genome, random integration often being state of the art. Lack of control over the position of introduced DNA results in unpredictable gene expression and potentially undesirable mutagenesis of important genes. A better solution would be a method that produces efficient site-specific integration into safe locations in the target genome. In these cases, conservative site-specific integration is important in genetic engineering strategies.

Enzymes of the site-specific recombination also share high specificity, and, in addition, they act with greater efficiency. Some recombinases function with no requirement for cofactors, permitting their activity in foreign cellular environments. Recombinases such as Cre and FLP perform both integration and excision with the same target sites (Sauer, B. (1994) Curr Opin. Biotechnol., 5, 521-527). Therefore, although these recombinases efficiently perform integration in mammalian cell, the net integration frequency that they mediate is low because of the excisive back reaction. To express the desired gene stably and efficiently at specific site, problems, such as low integration efficiency and stability, must be solved.

The present inventors have identified that integrase MJ1 from φFC1 of *enterococcus faecalis* is a good example in the efficiency and stability.

SUMMARY OF THE INVENTION

The present invention provides a recombinant vector containing MJ1 gene encoding integrase having an amino acid sequence of SEQ ID No. 2, wherein the integrase mediates site-specific integration but not mediates excision in animal cell.

Figure 1A:
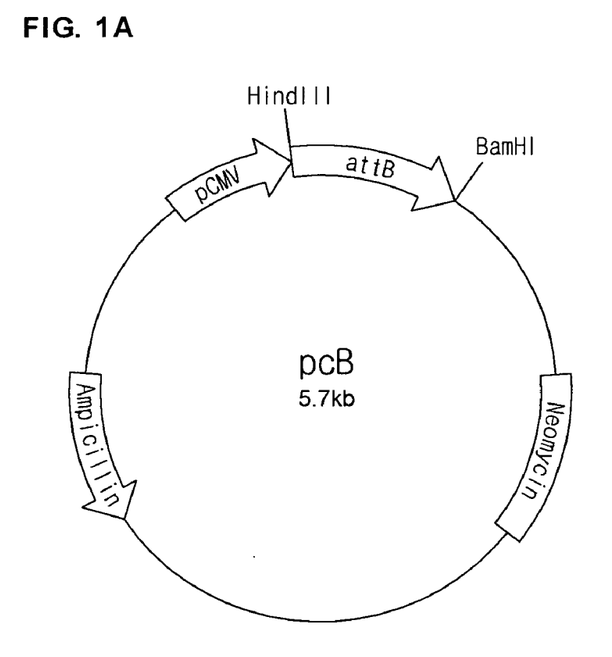
FIG. 1A is a plasmid map of pcB vector which comprises 290 bp attB gene and CMV promoter.
Figure 1B:
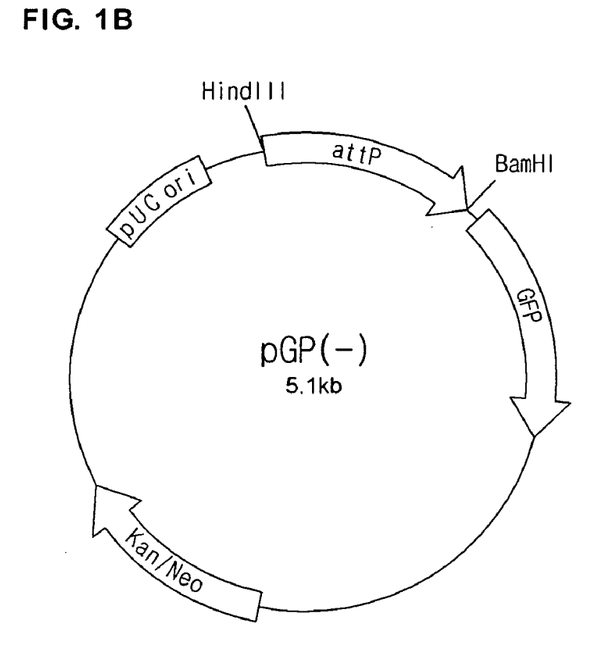
FIG. 1B is a plasmid map of pGP(-) vector which comprises 739 bp attP gene and includes not CMV promoter but GFP reporter gene.
Figure 1C:
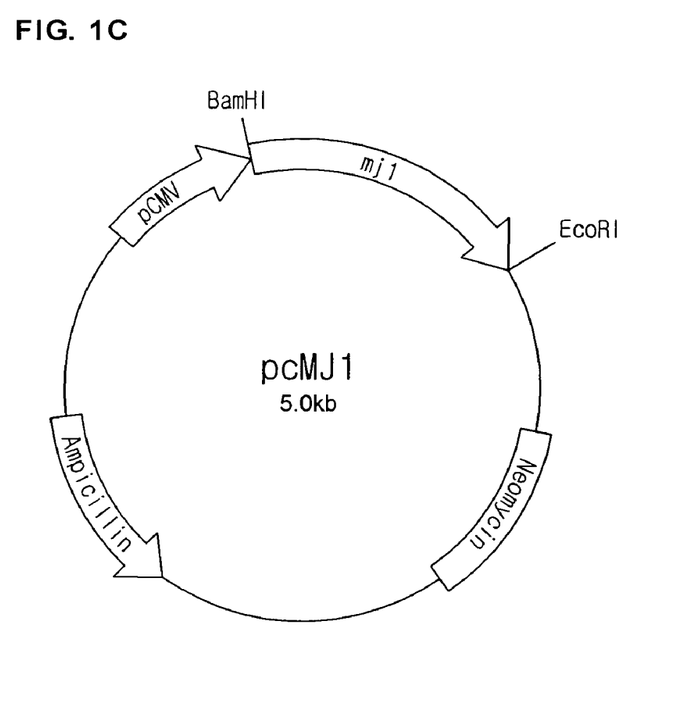
FIG. 1C is a plasmid map of pcMJ1 vector which comprises MJ1 gene of the present invention.

In the present recombinant vector according to claim 1, the MJ1 gene may have any base sequence capable of encoding integrase having an amino acid sequence of SEQ ID No. 2. Preferably, the MJ1 gene has a base sequence of SEQ ID No. 1 and the recombinant vector has a plasmid map shown in FIG. 1C.

The present invention provides a method of site-specific integration in animal cell, which comprises co-transfecting the animal cell with a recombinant vector containing MJ1 gene encoding integrase having an amino acid sequence of SEQ ID No. 2, a recombinant vector containing attB gene and a recombinant vector containing attP gene.

In the present method, the recombinant vectors may be any recombinant vector which has MJ1 gene, attB gene or attP gene. Preferably, the MJ1 gene has a base sequence of SEQ ID No. 1 and the recombinant vector containing MJ1 gene has a plasmid map shown in FIG. 1C.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in greater detail.

In the present invention, it is shown that integrase MJ1 of ϕFC1 from enterococcus faecalis also functions in human cells as well as E.coli. On extrachromosomal vector system, each plasmid which has attP, attB and integrase MJ1 coding sequence was constructed and cotransfected into human cell line HEK 293T (FIG. 1). The site-specific integration and excision reaction in trans, in the presence or absence of MJ1, was monitored by green fluorescent protein (GFP) as a reporter. Plasmids that carry attB (pcB) gene and integrase MJ1 coding gene (pcMJ1) have cytomegalovirus (CMV) promoter. However, plasmid (pGP(-)) harboring both attP and GFP couldn't express GFP because it does not have CMV promoter, so recombinant plasmid (pREC-I) could not be created. In this way, site-specific excision reaction could be observed when attP and attB is replaced with attL and attR.

In addition, it was confirmed that MJ1 integrase functions in human cell without any accessory factors on an extrachromosomal vector based system, and efficiency of integrase MJ1 was the better for no excision. Also, several hundred base pair of att site could be reduced to about 50 bp.

In the present invention, attP means the attachment site of the bacteriophage (739 bp) and attB means the attachment site of the bacterium (290 bp). And, attL and attR mean the left region (404 bp) and the right region (624 bp) which are created by site-specific recombination between attP and attB.

To clone the attB, a genomic DNA of the indicator strain of bacteriophage ϕFC, *Enterococcus faccalis* KBL707 strain (Accession No. KFCC 12177) deposited with Korean Culture Center of Microorganisms (KCCM), was used as a template of PCR. As for attL and attR, a genomic DNA of KBL703 strain (Kim et al. Mol. Cells 4; 155-158) of which chromosome was integrated with bacteriophage ϕFC was used as a template of PCR. As for attP, pFE1 which is inserted with 7.7 kb of ϕFC1 DNA (Kim and Y. W. 1999. Genetic studies of bacteriophage FC1 from *Enterococcus faecalis*. PH. D. Thesis. Korea University. Korea) was used as a template of PCR.

In the present invention, the base sequence of MJ1 gene was shown in SEQ ID No. 1 and the amino acid sequence of MJ1 integrase was shown in SEQ ID No. 2. Further, the base sequence of the attP gene was shown in SEQ ID No. 3 and the base sequence of the attB was shown in SEQ ID No.4.

Detection of minimal size at attP and attB site is valuable for taking advantage of efficiency strategy for gene therapy. Full length of 739 bp attP and 290 bp attB, already reported, are so long to utilize of useful gene therapy. Therefore nested deletion of attP and attB was performed based on MJ1 binding site at att to find the minimal size of aft site. These results demonstrate that efficient minimal size of attP and attB is 54 (160-233 of SEQ ID No. 3) and 48 bp (66-113 of SEQ ID No.4), and that the size is enough functional to integration by MJ1.

In the concrete examples of the present invention, the bacterium and bacteriophage were cultured, the plasmids containing MJ1 gene, attP or attB site were constructed, human fetus kidney cell line 293 was cotransfected with the plasmids, fluorescence activity of GFP reporter was measured, RT-PCR of MJ1 gene was performed in animal cell, FACS analysis was carried out, and integration of attP and attB and excision of attL and attR was confirmed.

EXAMPLES

The present invention now will be described in greater detail by means of the following examples. The following examples are for illustrative purpose and are not intended to limit the scope of the invention.

Example 1

Culture of Bacterium and Bacteriophage

*Enterococcus faecalis* KBL703 strain and KBL707 strain (Accession No. KFCC 12177) were cultured in Todd Hewitt broth (THB: Difco Co. U.S.A) at 37° C. without shaking. *E.coli* (DH5α) was cultured in LB at 37° C. with shaking. Temperate bacteriophage ϕFC1 was inducted from *Enterococcus faecalis* KBL703 with UV-radiation and purified. The bacteria strains and plasmids used in this invention was listed in the below Table 1.

TABLE 1

| Strains or Plasmids | | Characteristics |
|---|---|---|
| *Enterococcus faccalis* | KBL703 | Lysogenic strain of φFC1 phage |
| | KBL707 | Indicator strain of φFC1phage |
| *Escherichia coli* | DH5α | supE44, ΔlacU169, hsdR17, recA1, endA1, gyrA96, thi-1, relA1 |
| Plasmid | pcDNA3 | mammalian cell expression vector, Ampr, Neor, replicative ori of Col1, promoter of CMV, T7, Sp6, SV40 |
| | pEGFP-N1 | mammalian cell expression vector, Kanr, Neor, replicative ori of pUC, promoter of CMV, HSV, TK, SV40e, GEP exp |
| | pG(-) | pEGFP-N1 deleting PCMV |
| | pGP(+) | pEGFP-N1 carrying 739 bp attP fragment |
| | pGP(-) | pG(-) carrying 739 bp attP fragment |
| | pcB | pcDNA3 carrying 290 bp attB fragment |
| | pGR(-) | pG(-) carrying 404 bp attR fragment |
| | pGR(+) | pEGFP-N1 carrying 404 attR fragment |
| | pcL | pcDNA3 carrying 624 bp attL fragment |
| | pcMJ1 | pcDNA3 carrying mj1 |

Example 2

Construction of Plasmids for Transfection to Animal Cell

Figure 1D:
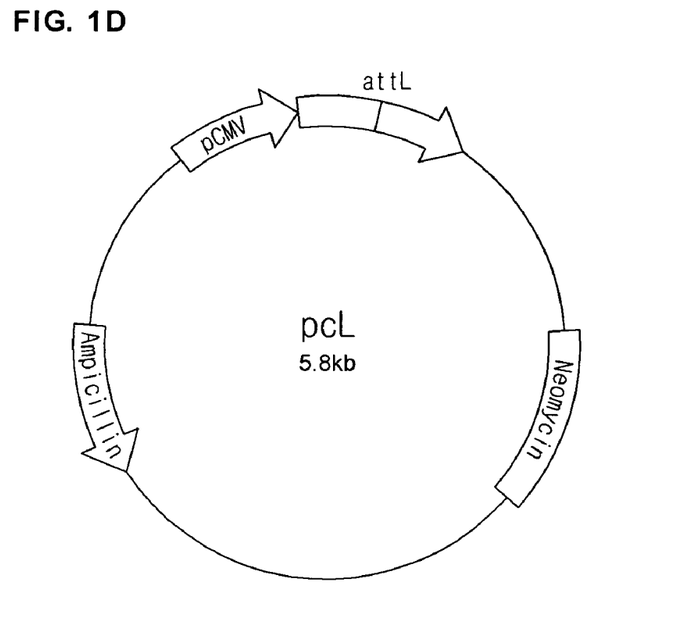
FIG. 1D is a plasmid map of pcL vector which comprises 624 bp attL gene and CMV promoter.
Figure 1E:
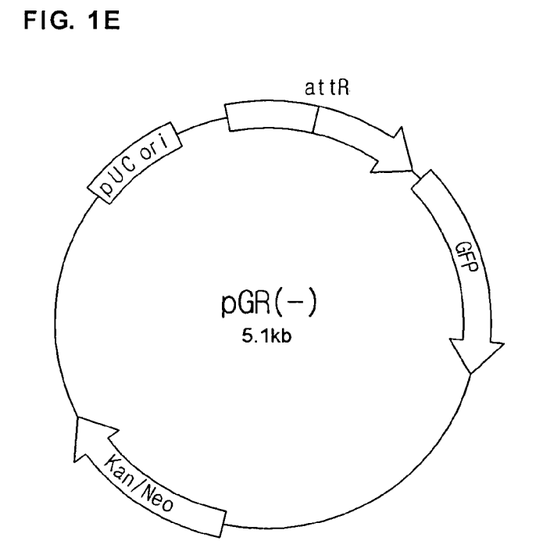
FIG. 1E is a plasmid map of pGR(-) vector which comprises 404 bp attR gene and includes not CMV promoter but GFP reporter gene.
Figure 1F:
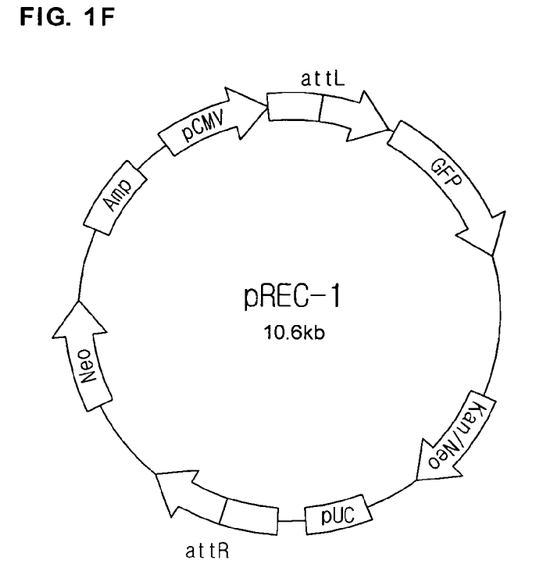
FIG. 1F is a plasmid map of pREC-1 vector which is formed by integration due to co-transfection with PcB, pGP(-) and pcMJ1.
Figure 1G:
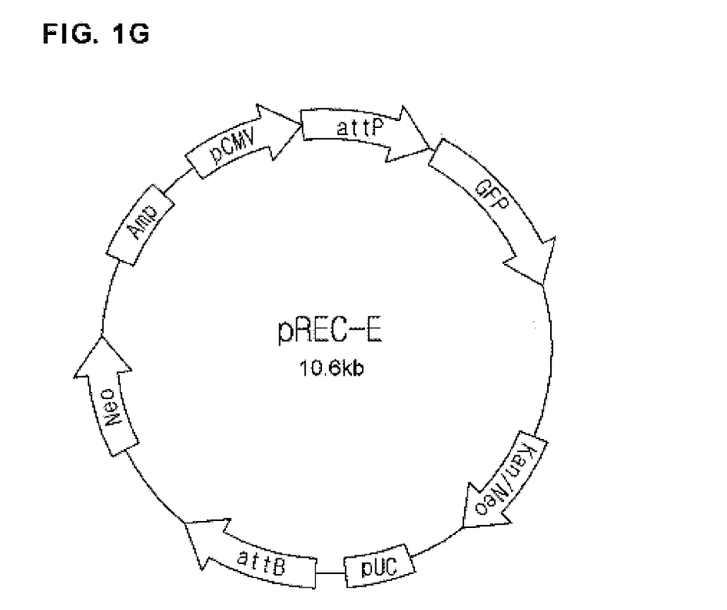
FIG. 1G is a plasmid map of pREC-E vector which may be formed by exision due to co-transfection with PcL, pGR(-) and pcMJ1.

To synthesize the MJ1 intergrase gene of about 1500 bp, attB gene of 290 bp and attL gene of 347 bp, PCR reactions were performed using DNA of bacteriophage cPFC1 and genomic DNA of KBL707 and KBL703 as templates and primers shown in the below Table 2. The PCR products were subcloned between BamHI and EcoRI sites or HindIII and BamHI sites of pcDNA3 (Invitrogen Carsbad, Calif.) to construct pcMJ1 (FIG. 1C), pcB (FIG. 1A) and pcL (FIG. 1D).

Plasmid pG(-) was created by deleting its small NdeI-BglII fragment from pEGFP-N1 (ClonTech, Palo Alto, Calif.) and blunt-end self ligation using klenow treatment. Plasmids pGP(-) (FIG. 1B) and pGR(-) (FIG. 1E) were made by subcloning the attP and attR PCR products amplified with primers shown in the below Table 2. Synthetic oligonucleotides used as primers in this invention are listed in Table 2.

Example 3

Transfection and Fluorescence Microscopy

Human embryonic kidney 293T cells (American Type Culture Collection, Manassas, Va.) were grown in Dulbecco's modified Eagle's medium (DMEM) supplemented with 10% heat-inactivated fetal bovine serum (FBS) and 100 U/ml penicillin in 100-mm plates. Cells were split into eight six-well culture plates or 60-mm plates and grown, until they were about 50% confluent. Plasmids prepared in Example 2 that carry attP, attB and MJ1 coding sequence were transfected in equimolar amounts (6 μg or 3 μg of total DNA) by using the calcium phosphate method.

The transfected cells were grown on cover slip placed in a six- well culture plates. After 72 h incubation the cells were examined under the confocal fluorescence microscope (Zeiss) for the expression of GFP. The efficiency of transformation was determined by the percentage of fluorescing cells in the transfected cells.

Example 4

Reverse Transcription-PCR (RT-PCR)

Figure 2:
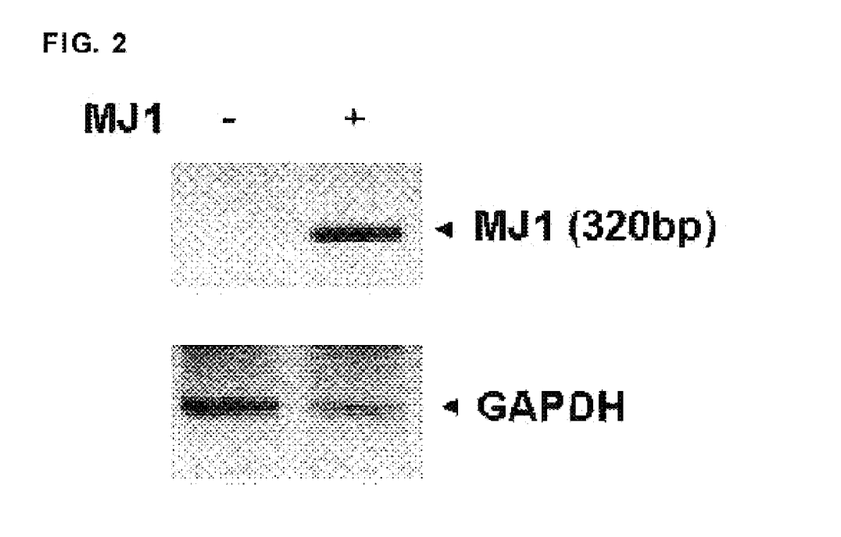
FIG. 2 is an image showing MJ1 expression in 293T cell.

Total RNA was extracted from pcMJ1 transfected 293T cell using TRIzol reagent (Invitrogen). Reverse transcription and PCR amplification were performed using SUPERSCRIPT II RNaseH-reverse transcriptase (Invitrogen) and pfu DNA polymerase (Promega). The level of expression of GAPDH gene served as internal control and the sequences of the primers were described in Table 2. PCR was performed for 25 cycles at 94° C. for 5 min, 94° C. for 20 s, 52° C. for 30 s, and 68° C. for 40 s. The PCR products were analyzed on a 1.5% agarose gel and stained with ethidium bromide for visualization. As shown in FIG. 2, expression level of MJ1 mRNA was elevated considerably as compared

TABLE 2

| | Sense | Antisense |
|---|---|---|
| MJ1 | CGGGATCCATGAAACGTGCAGCATTG | CGGAATTCACCGAATGCATGTTCGTA |
| attP | CGGAATTCACCGAATGCATGTTCGTA | GCGTTAACTGCCAATATAGC |
| attB | CGGCCATTGAATTAGGGTGTCGAAT | CGGATTGCCAGATGGATGAT |
| attL | CGCAAGCTTGAAACGTTAAAAACTTTTAAT | CGGGATCCCGGCCATTGAATTAGGGTGTC |
| attR | CGCAAGCTTCGGATTGCCAGATGGATGATT | CGGGATCCGAAGATCTTGTTCTCGAGCAT |
| MJ1RT | GGAAATCAATTAGGGCTTTT | TCGTTATGCTTCTTGGAAAT |
| GAPDH | CATCTCTGCCCCCTCTGCTG | CGACGCCTGCTTCACCACCT |

The sequences disclosed above in Table 2 are identified as follows:

MJ1, Sense, is SEQ ID NO:5; attP, Sense, is SEQ ID NO:7; attB, Sense, is SEQ ID NO:9; attL, Sense, is SEQ ID NO:11; attR, Sense, SEQ ID NO:13; MJ1RT, Sense, SEQ ID NO:15; GAPDH, Sense, SEQ ID NO:17; MJ1, Antisense, is SEQ ID NO:6; attP, Antisense, is SEQ ID NO:8; attB, Antisense, is SEQ ID NO:10; attL, Antisense, is SEQ ID NO:12; attR, Antisense, SEQ ID NO:14; MJ1RT, Antisense, SEQ ID NO:16; and GAPDH, Antiense, SEQ ID NO:18.

to that of the internal control gene GAPDH. The PCR generated a 320 bp product with specific primer pair for the MJ1 coding region (FIG. 2). RT-PCR showed that integrase MJ1 is ectopically expressed in human cell.

Example 5

Fluorescent-Activated Cell Sorting (FACS) Analysis

FACS was performed for the expression of GFP. 72 hr post-transfection, cells were harvested, resuspended with 3 ml of 5 mM EDTA/PBS and washed twice, and then fixed in 300 μl of 0.1% BSA and 0.05% NaN3/PBS. FACS was performed on a FACScan analysis (Becton Dickinson Immunocytometry Systems) using the CellQuest program (Becton Dickinson).

Below, the experimental result which verifies the result of the above-mentioned examples of this invention is disclosed.

Experimental Example 1

Site-specific Integration or Excision

Figure 3:
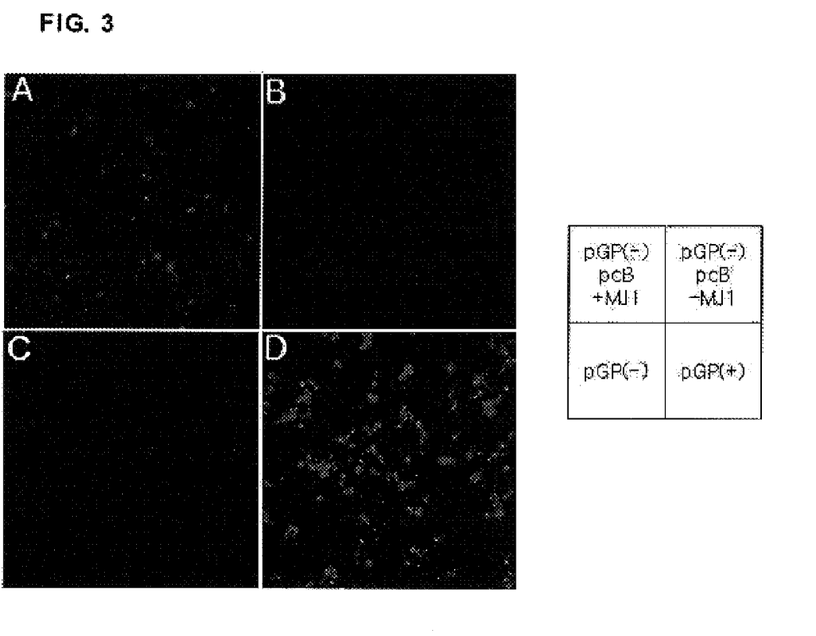
FIG. 3 is an image of confocal microscope showing integration results in 293T cell.
Figure 4A:
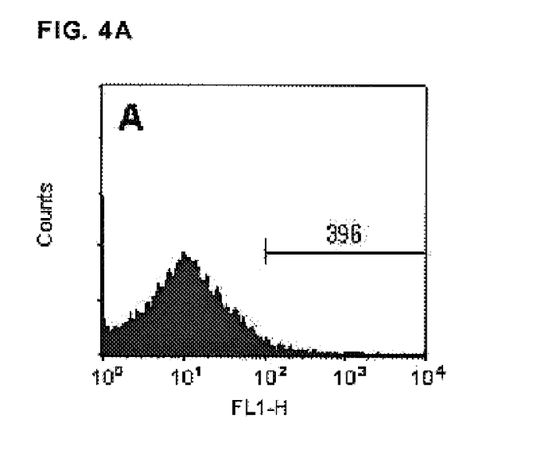
FIG. 4A is a FACS data showing GFP expression without MJ1. (Y-axis is cell number and X-axis is GFP expression level)
Figure 4B:
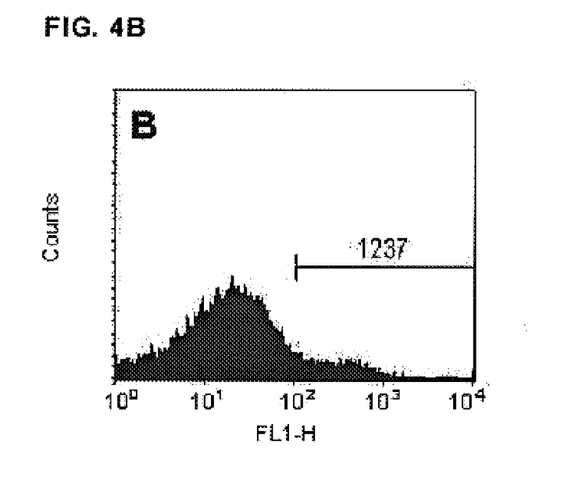
FIG. 4B is a FACS data showing GFP expression with MJ1. (Y-axis is cell number and X-axis is GFP expression level)
Figure 4C:
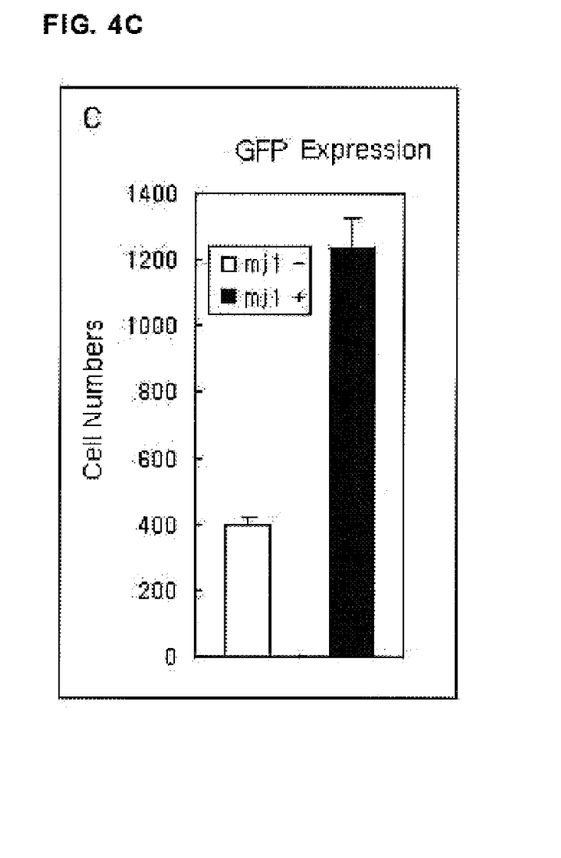
FIG. 4C is a graph showing quantized numerical values of FIG. 4A and 4B.
Figure 5:
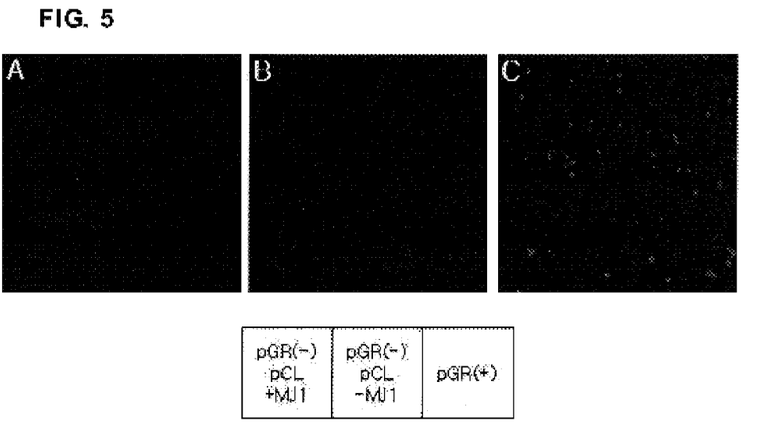
FIG. 5 is an image of confocal microscope showing excision results in 293T cell.

Different constructs could monitor either the integration reaction (attP×attB) or the excision (attL×attR). To determine effect of MJ1 on the reaction of integration, 293T cells were cotransfected with plasmids pcB and pGP(−), together with pcMJ1 or without pcMJ1. After 72 hr, cells were observed by confocal microscope. In the case of plasmid pREC-1 (FIG. 1F) created by MJ1-mediated integration, expression of GFP only occurred (FIG. 3A). In contrast, GFP expression was not observed in the cell cotransfected without MJ1 expectably (FIG. 3B). To show that each cases was not owing to promoter, cells that were transfected with plasmid pGP(+) or pGP(−) with or without CMV promoter, respectively, were also observed by confocal microscope (FIGS. 5C and 5D). As expected, GFP expression was not investigated in cell transfected with only pGP(−). To search integration efficiency, the 293T cells were transfected with plasmids pcB and pGP(−) together with or without MJ1 expressing plasmid pcMJ1 and 72 hr after transfection the cells underwent a FACS analysis. Histogram plots that depict the fluorescence of transfected cells in the absence or presence of MJ1 are shown in FIGS. 4A and 4B. Cells transfected with plasmids that carry att sites along, in the absence of MJ1, showed a fluorescence of 396 cells (FIG. 4A). In contrast, in the presence of MJ1 the cell number of fluorescence was 1237 in the integration reaction, so their gap came up to about 4 times as shown FIG. 4C.

In the case of excision, plasmids that carry attR (pGR(−)) and attL (pGL) instead of pGP(−) and pcB were cotransfected into 293T cell. As a result, GFP expression was not observed in contrast to integration (FIG. 5A). To prove that the result was not caused by promoter, cells transfected with plasmid pGR(+) or pGR(−), with or without CMV promoter, respectively, were observed by confocal microscope. pGR (+), but not pGR(−) showed GFP activity (FIGS. 5B and 5C). This result means that putative recombinant plasmid pREC-E (FIG. 1G) was not created by MJ1. It is shown that MJ1-catalyzed excision does not occur between attL and attR.

It is demonstrated that MJ1 mediates site-specific integration between attP and attB efficiently in human cell on an extrachromosomal vector base, but MJ1-catalyzed excision does not occur between attR and attL.

Experimental Example 2

Determination of Minimal Size of attB and attP

Figure 6:
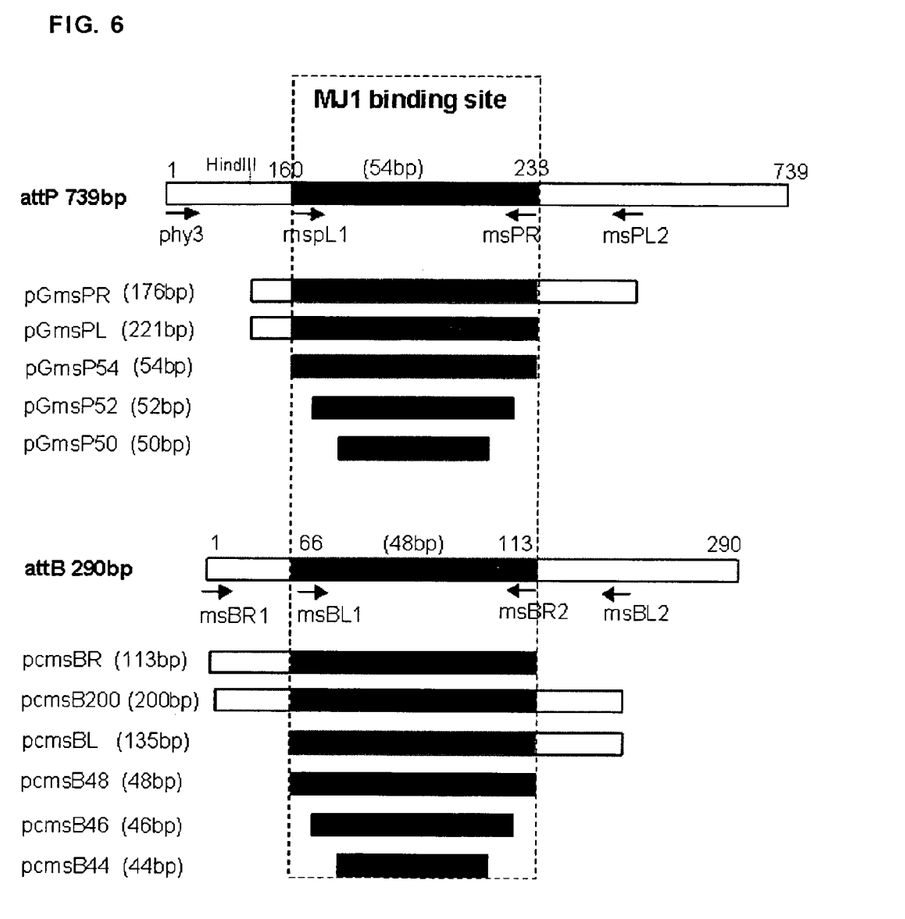
FIG. 6 is a schematic diagram showing nested deletion of attP and attB.

Before this invention, no information about minimal size of attB and attP sites on which the MJ1 functions had been reported. To minimal functional sizes for these att sites, site-specific integration assay system described above was performed using nested set of deletion clones of attB and attP (FIG. 6). Each plasmid that carries deleted site bearing 3 bp conserved core sequences was made by nested deletion centering around the site known for MJ1 binding. Short double-stranded adaptor molecules containing att sites of various lengths were created by annealing single-stranded oligonucleotides. These deleted sites were used to replace the full-length att sites in the pGP(−) and pcB plasmids, the plasmids were cotransfected with or without pcMJ1 and integration efficiencies were determined by FACS analysis.

Figure 7:
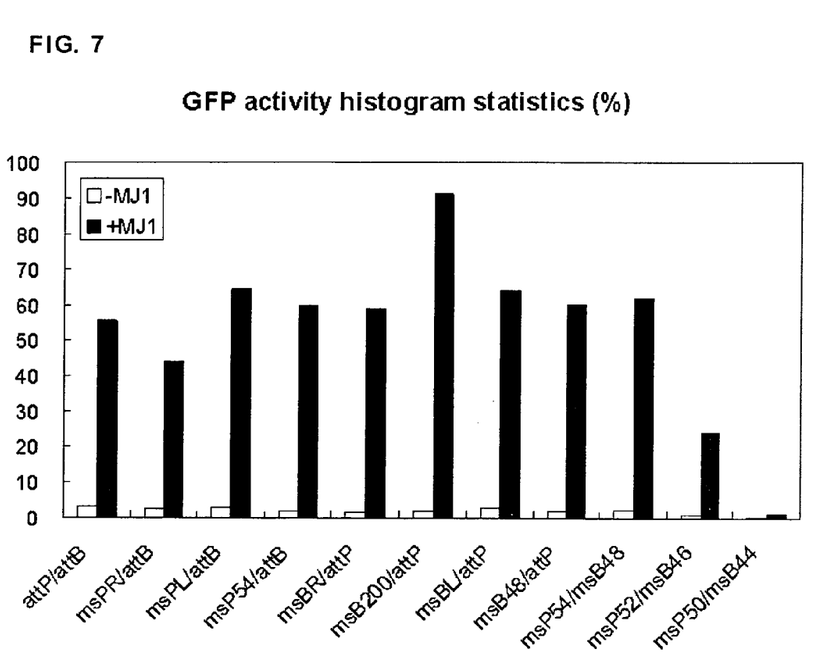
FIG. 7 is a graph showing integration efficiency due to size of attP and attB site.

As a result, integration efficiency owing to size of attP and attB site was indicated as FIG. 7. The discrepancy of cell that transfected with or without plasmid pcMJ1 was graphed to % numerical value. The integration efficiency was not been decreased in proportion to reduction attP and attB site. However, the efficiency of integration was gradually decreased from integration efficiency between 54 bp attP and 48 bp attB. In the final analysis, almost integration functions were lacked between 50 bp attP and 44 bp attB. These results demonstrate that efficient minimal size of attP and attB is 54 (160-233 of SEQ ID No. 3) and 48 bp (66-113 of SEQ ID No. 4), and that the size is enough functional to integration by MJ1.

Integrase MJ1 has lots of advantage to construct gene transfer system than any other viral vector or existing gene transfer system.

First, MJ1 does not need any requirements for E.faecalis-specific cofactor for site-specific integration. In contrast, λ integrase requires IHF for both type of recombination and IHF is required in many types of recombination, including that of phage HK022 and HP1 (Dorgai et al., (1998) J. Mol. Biol., 277, 1059-1070). This invention demonstrates that site-specific integration in human cell occurred between attP and attB with only integrase MJ1 without any cofactor as observing GFP expression.

Second, unlike other integrases (recombinases) from phage which mediate both integration and excision, integrase MJ1 was shown to only have integration function. It was reported that integrase (recombinase) from phage HK022 could perform both integrative (attP/attB) and excisive (attL/attR) recombination in mouse NIH3T3 cells (Kolot et al., (1999) Mol. Biol. Rep., 26, 207-213). In this invention, MJ1 only mediates the integration function, and that integrated gene was not excised from host genome, so desired gene could be expressed continuously.

Third, it was shown that 48-bp and 54-bp minimal sizes for the attB and attP sites enabled MJ1 to mediate the integration. It appears that this integration may be done at naturally occurring pseudo-att sites in eukaryotic genomes having significant similarity to native att sequences (Thyagarajan et al., (2000) Gene, 244). The expected rarity of good matches with att sites may limit recombination to a small number of chromosomal pseudo-att sites, which may produce usable integration frequencies at endogenous locations in the chromosomes.

Besides these advantages, MJ1-mediated site-specific integration system is profitable for development of gene transfer system. The probability that has an effect on expres sion of essential genes or/and on interference of host cell mechanism was decreased certainly because this system get inserted gene to integrate into pseudo-site on host genomic DNA. Also integrase from phage could transfer more than ten kilo-base pair of insertion gene into target site, allowing for the several tens of kb-sized of phage congestion, because phages can transfer integrated their whole phage genome into bacterial genome using its integrase by nature.

What is claimed is:

1. A recombinant vector containing an MJ1 gene encoding an integrase having an amino acid sequence of SEQ ID No. 2, wherein the integrase mediates site-specific integration but does not mediate excision in animal cells, and the recombinant vector has a plasmid map shown in FIG. 1C.

2. The recombinant vector according to claim 1, wherein the MJ1 gene has a base sequence of SEQ ID No. 1.

3. A method of site-specific integration in an animal cell, which comprises co-transfecting the animal cell with a recombinant vector containing MJ1 gene according to claim 1, a recombinant vector containing an attB genes and a recombinant vector containing an attP gene.

4. The method according to claim 3, wherein the MJ1 gene has a base sequence of SEQ ID No. 1.

* * * * *